United States Patent [19]

Grab

[11] Patent Number: 4,775,533

[45] Date of Patent: Oct. 4, 1988

[54] RECONSTITUTION OF DRY FILL CYCLOPHOSPHAMIDE

[75] Inventor: Frederick L. Grab, Dublin, Ohio

[73] Assignee: Erbamont, Inc., Dublin, Ohio

[21] Appl. No.: 18,217

[22] Filed: Feb. 24, 1987

[51] Int. Cl.$^4$ .......................... A61B 17/06; A61B 19/02
[52] U.S. Cl. ..................................... 424/451; 424/489; 206/524.1; 206/219; 206/438
[58] Field of Search ............................... 424/451, 489; 206/524.1, 219, 438

[56] References Cited

PUBLICATIONS

1983 *Physicians' Desk Reference*, Medical Economics Company, Inc., Oradell, 1983, p. 1214.

*Primary Examiner*—Nancy A. B. Swisher
*Attorney, Agent, or Firm*—Smith & Schnacke

[57] ABSTRACT

In a method for reconstituting dry fill cyclophosphamide, the vial volume is at least 50 ml and the headspace is at least 15 ml.

5 Claims, No Drawings 4,775,533

RECONSTITUTION OF DRY FILL CYCLOPHOSPHAMIDE

BACKGROUND OF THE INVENTION

The present invention relates to dry fill cyclophosphamide and to a method of reconstituting dry fill cyclophosphamide.

Cyclophosphamide has been used to inhibit cell growth in the treatment of malignant growths and similar diseases. Clinical tests have proven that cyclophosphamide is effective as an antineoplastic agent.

cyclophosphamide is available under the trademark Cytoxan from Bristol-Myers Oncology Division of Bristol-Myers Company. Bristol-Myers supplies Cytoxan in a 20 ml vial for a 200 mg dosage and a 30 ml vial for a 500 mg dosage. The solvent volume recommended for the 200 mg vial is 10 ml while the solvent volume recommended for the 500 mg vial is 25 ml.

The current reconstitution method for dry fill cyclophosphamide involves adding solvent to a vial containing a unit dosage of dry fill cyclophosphamide. The solution is agitated to reconstitute the dry fill cyclophosphamide which is then withdrawn for injection. This method has proven to be unsatisfactory for unit dosages of 500 mg or greater because the reconstitution time of the dry fill cyclophosphamide powder is lengthy.

DEFINITIONS

The term "headspace" as used herein means the difference between the complete vial volume and solvent volume for reconstitution.

SUMMARY OF THE INVENTION

An object of the present invention is to provide a method for reconstituting dry fill cyclophosphamide for use in injections without having to resort to the expense of providing a lyophilized product.

A further object of the present invention is to provide a dry fill cyclophosphamide in unit dosage form to be reconstituted for use in injections.

An additional object of the present invention is to decrease the reconstitution time required for large dosages of dry fill cyclophosphamide and thereby minimize a potential safety hazard.

In accordance with the present invention, a method is provided for reconstituting dry fill cyclophosphamide for use in injections which comprises the steps of:
  placing a unit dosage of dry fill cyclophosphamide in a vial having a volume of at least 50 ml;
  adding solvent to the dry fill cyclophosphamide in the vial so that the headspace is at least 15 ml;
  agitating the dry fill cyclophosphamide in the solvent to dissolve the dry fill cyclophosphamide; and
  withdrawing the reconstituted cyclophosphamide in preparation for injection.

The present invention also provides a dry fill cyclophosphamide in unit dosage form to be reconstituted for use in injections which comprises a unit dosage of at least 500 mg. dry fill cyclophosphamide in a vial having a nominal volume greater than about 50 ml.

Other objects and advantages of the present invention will become apparent from the following description and the appended claims.

DETAILED DESCRIPTION OF THE INVENTION

Any commercially available vial is useful in the present invention. A vial having a nominal volume of at lest 50 ml., typically provides sufficient headspace after addition of the solvent to the 500 mg dry fill cyclophosmide in order to decrease the reconstitution time required. Preferably, the vial has a volume of about 50 to 250 ml.

Useful examples of commercially available vials are listed in the following Table:

| Manufacturer | Commercially Available Vials | | | |
| --- | --- | --- | --- | --- |
| | Capacity (Base of Neck, ml) | Diameter (Approx. mm) | Height (Approx. mm) | Mold # |
| Kimble | 32.0–34.0 | 31 | 73 | CA-8397 |
| Kimble | 56.7–60.3 | 43 | 73 | CA-8299 |
| Kimble | 68.7–72.3 | 44 | 80 | CA-8160 |
| Kimble | 116.4–122.4 | 52 | 94 | CA-8946 |
| Kimble | 151.8–158.2 | 54 | 106 | CA-8149 |
| Wheaton | 39.3 | 34 | 74 | S-114 |
| Wheaton | 71 | 41 | 91 | S-326 |
| Wheaton | 146 | 49 | 125 | M-236B |
| Nuova Ompi S.p.A. | 50–80 | 35.5 | 116 | — |
| Vetreria Bormioli S.p.A. | 73 | 46 | 72.5 | — |

Dry fill cyclophosphamide is available under the trademark Neosar from Adria Laboratories, Inc. Standard cyclophosphamide unit dosages are 100 mg, 200 mg, 500 mg and 1 gm. Both Adria Laboratories, Inc. and Bristol-Myers Company supply cyclophosphamide in sealed vials ready for reconstitution.

To achieve the objects of the present invention, the headspace of the vial must be carefully controlled. Typically, the headspace is at least 15 ml. It has been found that for 500–1000 mg dosages of cyclophosphamide, if the headspace is less than about 15 ml, the decreased headspace allowed for agitation of the solution in the vial results in a longer reconstitution time. Preferably, the headspace is at least 25 ml and more particularly, the headspace is at least 35 ml.

Any conventionally used means for adding solvent to a vial is useful in the present invention. Typically, the solvent is injected into the vial.

Any solvent which is conventionally used in reconstituting dry fill cyclophosphamide is useful in the present invention. Water for injection is an example of a typical solvent.

The solvent of the dry fill cyclophosphamide in solvent is agitated to reconstitute the dry fill cyclophosphamide. Any conventionally used means for agitating a solution of a powdered drug and solvent in a vial is useful in the present invention. A mechanical shaker is particularly useful in reconstituting the dry fill cyclophosphamide of the present invention.

The reconstituted cyclophosphamide is then withdrawn from the vial in preparation for an injection. Typically, a syringe is inserted into the vial to withdraw the reconstituted cyclophosphamide.

The present invention is more fully illustrated by the following non-limiting Examples.

EXAMPLE 1

Reconstitution times were determined for two lots of 500 mg doses of Neosar with 30 ml and 50 ml vials and two lots of 1 gm doses of Neosar with 50 ml and 75 ml vials. Each lot contained ten vials. For each vial, 25 ml of water were added to the dry fill cyclophosphamide in the vial. Each vial was mechanically shaken for 15 seconds and inspected for 15 seconds. This cycle was repeated until the contents were completely dissolved. The reconstitution time was determined by multiplying the number of cycles by 15 seconds.

Tables 1 and 2 contain a statistical work up of the reconstitution time after reconstitution of each vial. For the reconstitution time for every vial, the statistics were calculated in the same manner. N was the population size. The Mean was calculated by adding the ten values and dividing by ten. The Standard Deviation (S.D.) was calculated by taking the square root of the variance which is the mean of the sum of the squared deviations. The Range represented the interval between the lowest and the highest values. The t value was calculated by multiplying the difference between the sample mean and population mean by the square root of the sample size and dividing by the sample deviation. The p value was the probability that t exceeded a certain value.

TABLE 1

Neosar 500 mg/30 ml vial vs. Neosar 500 mg/50 ml vial
Reconstitution Time (Minutes)

| Vial Size | Lot No. | N | Mean | S.D. | Range | t | P |
|---|---|---|---|---|---|---|---|
| 30 ml | 1 | 10 | 9.60 | 1.91 | 7.00–12.75 | 10.88 | .0001 |
| 50 ml | 2 | 10 | 2.43 | 0.83 | 1.50–3.75 | | |

Table 1 illustrates that a significant difference exists between the two lots. The reconstitution time of the Neosar 500 mg/30 ml vial was nearly four times greater than that of the Neosar 500 mg/50 ml vial.

TABLE 2

Neosar 1 gram/50 ml vial vs. Neosar 1 gram/75 ml vial
Reconstitution Time (Minutes)

| Vial Size | Lot No. | N | Mean | S.D. | Range | t | P |
|---|---|---|---|---|---|---|---|
| 50 ml | 3 | 10 | 15.78 | 6.25 | 5.75–25.00 | 6.04 | .0001 |
| 75 ml | 4 | 10 | 3.83 | 0.26 | 3.25–4.25 | | |

Table 2 illustrates that a significant different exists in the reconstitution times of the two lots. The reconstitution time for the Neosar 1 gram/50 ml vial was four times greater than that of the Neosar 1 gram/75 ml vial.

In each case, in comparing lots of Neosar of the same strength using different sized vials, lots with the larger vials dissolved significantly faster than lots with the smaller vials.

COMPARATIVE EXAMPLE

For comparative purposes, the reconstitution times of Adriamycin, registered trademark, were determined for two different fill sizes (25 mg/50 ml vial and 50 mg/50 ml vial). Ten vials per fill size were used in the study. The 25 mg/50 ml fill size was reconstituted with 12.5 ml of 0.9% sodium chloride, USP and the 50 mg/50 ml fill size was reconstituted with 25 ml of 0.9% sodium chloride, USP. As was done previously in Example 1, each vial was mechanically shaken for 15 seconds and inspected for 15 seconds. This cycle was repeated until the contents were completely dissolved. The dissolution time was determined by multiplying the number of cycles by 15 seconds. The appearance of each vial was determined after dissolution. Reconstitution time (min.) and appearance were recorded for each vial (Table 3).

TABLE 3

| Reconstitution Time (Minutes) | Appearance |
|---|---|
| 25 mg/50 ml vial | |
| 8.00 | normal |
| 6.75 | normal |
| 6.25 | normal |
| 6.00 | normal |
| 6.25 | normal |
| 8.50 | normal |
| 5.75 | normal |
| 7.00 | normal |
| 7.75 | normal |
| 6.75 | normal |
| 50 mg/50 ml vial | |
| 11.50 | normal |
| 8.50 | normal |
| 9.25 | normal |
| 7.50 | normal |
| 9.25 | normal |
| 8.25 | normal |
| 11.75 | normal |
| 10.00 | normal |
| 11.75 | normal |
| 11.00 | normal |

A two-sample student's t-test was used to compare the reconstitution time of the two samples. The statistical analysis (Table 4) indicates that a significant difference between the two lots exists. The reconstitution time of Adriamycin 50 mg/50 ml is nearly one-half times greater than that of Adriamycin 25 mg/50 ml.

TABLE 4

Statistical Analysis
Reconstitution Time (minutes)

| Product | Vial Size | N | Mean | S.D. | Range | t | P |
|---|---|---|---|---|---|---|---|
| Adriamycin 25 mg | 50 ml | 10 | 6.90 | 6.91 | 6.00–8.00 | 5.20 | less than .01 |
| Adriamycin 50 mg | 50 ml | 10 | 9.88 | 1.56 | 7.50–11.75 | | |

Although an increase in the headspace to product ratio results in a statistically significant decrease in reconstitution time, the actual difference in average reconstitution time is about 3 minutes (30% decrease) as compared to a decrease in the reconstitution time of cyclophosphamide by 7 minutes (75% decrease) (Neosar: 500 mg/30 ml vial vs 50 mg/50 ml vial) and 12 minutes (76% decrease) (Neosar: 1 g/50 ml vial vs 1 g/75 ml vial).

Having described the invention in detail and by reference to preferred embodiments thereof, it will be apparent that modifications and variations are possible without departing from the scope of the invention defined in the appended claims.

What is claimed is:

1. A dry fill cyclophosphamide in unit dosage form to be reconstituted for use in injections which comprises a unit dosage of said dry fill cyclophosphamide in a vial having a volume of about 50 ml or greater and providing a headspace of at least 25 ml when said vial is filled with a solvent for reconstitution.

2. The dry fill cyclophosphamide of claim 1 wherein the volume of said vial is about 50 to 250 ml.

3. The dry fill cyclophosphamide of claim 2 wherein said unit dosage of said dry fill cyclophosphamide is about 500 mg or greater.

4. A method for reconstituting dry fill cyclophosphamide for use in injections which comprises the steps of:

placing a unit dosage of said dry fill cyclophosphamide in a vial having a volume of at least 50 ml;

adding solvent to said dry fill cyclophosphamide in said vial so that the headspace is at least 25 ml;

agitating said dry fill cyclophosphamide in said solvent to reconstitute said dry fill cyclophosphamide; and withdrawing said reconstituted cyclophosphamide in preparation for injection wherein said solvent is added to said dry fill cyclophosphamide in said vial such that the headspace is at least 25 ml.

5. The method of claim 4 wherein said unit dosage of said dry fill cyclophosphamide is greater than about 500 mg.

* * * * *